United States Patent
Lalvani et al.

(10) Patent No.: US 7,572,597 B2
(45) Date of Patent: Aug. 11, 2009

(54) DIAGNOSTICS METHOD

(75) Inventors: Ajit Lalvani, Oxford (GB); Katie Ewer, Oxford (GB)

(73) Assignee: Isis Innovation Limited, Oxford (GB)

( * ) Notice: Subject to any disclaimer, the term of this patent is extended or adjusted under 35 U.S.C. 154(b) by 371 days.

(21) Appl. No.: 10/520,084

(22) PCT Filed: Jul. 7, 2003

(86) PCT No.: PCT/GB03/02936

§ 371 (c)(1),
(2), (4) Date: May 6, 2005

(87) PCT Pub. No.: WO2004/005925

PCT Pub. Date: Jan. 15, 2004

(65) Prior Publication Data

US 2005/0208594 A1    Sep. 22, 2005

(30) Foreign Application Priority Data

Jul. 5, 2002   (GB) ................... 0215710.5

(51) Int. Cl.
*G01N 33/554* (2006.01)
(52) U.S. Cl. .................... 435/7.32; 435/4; 435/7.1; 435/7.92; 530/300; 530/350; 424/248.1
(58) Field of Classification Search .......... 435/4, 435/7.1, 7.32, 7.92; 530/300, 350; 424/248.1
See application file for complete search history.

(56) References Cited

FOREIGN PATENT DOCUMENTS

| WO | WO 00/26248 | 5/2000 |
|----|-------------|--------|
| WO | WO 01/04151 | 1/2001 |
| WO | WO 02/054072 | 7/2002 |

OTHER PUBLICATIONS

Mikayama et al. (Nov. 1993. Proc.Natl.Acad.Sci. USA, vol. 90 : 10056-10060).*

Lalvani et al. "Enhanced contact tracing and spatial tracking of mycobacterium tuberculosis infection by enumeration of antigen-specific T cells" The Lancet 357:2017-2021 (2001).

Pathan et al. "Direct ex vivo analysis of antigen-specific IFN-gamma-secreting CD4 T cells in mycobacterium tuberculosis-infected individuals: Associations with clinical disease state and effect of treatment" J. Immunol. 167:5217-5225 (2001).

* cited by examiner

*Primary Examiner*—Jennifer E Graser
(74) *Attorney, Agent, or Firm*—Nixon & Vanderhye P.C.

(57) ABSTRACT

Method of diagnosing in an individual recent exposure to an agent which is a pathogen, vaccine or any other moiety which induces a cellular response, said method comprising determining in vitro whether the T cells of the individual recognise a protein from said agent having a length of at least 30 amino acids, to a greater extent than one or more peptide epitopes from the agent, a greater extent of recognition of the protein indicating that the individual has recently been exposed to the agent.

6 Claims, No Drawings

SEQUENCE LISTING

<160> NUMBER OF SEQ ID NOS: 37

<210> SEQ ID NO 1
<211> LENGTH: 15
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala
1               5                   10                  15

<210> SEQ ID NO 2
<211> LENGTH: 15

```
<212> TYPE: PRT
<213> ORGANISM: Mycobacterium tuberculosis

<400> SEQUENCE: 2

Trp Asn Phe Ala Gly Ile Glu Ala Ala Ala Ser Ala Ile Gln Gly
1               5                   10                  15

<210> SEQ ID NO 3
<211> LENGTH: 15
<212> TYPE: PRT
<213> ORGANISM: Mycobacterium tuberculosis

<400> SEQUENCE: 3

Ile Glu Ala Ala Ala Ser Ala Ile Gln Gly Asn Val Thr Ser Ile
1               5                   10                  15

<210> SEQ ID NO 4
<211> LENGTH: 15
<212> TYPE: PRT
<213> ORGANISM: Mycobacterium tuberculosis

<400> SEQUENCE: 4

Ser Ala Ile Gln Gly Asn Val Thr Ser Ile His Ser Leu Leu Asp
1               5                   10                  15

<210> SEQ ID NO 5
<211> LENGTH: 15
<212> TYPE: PRT
<213> ORGANISM: Mycobacterium tuberculosis

<400> SEQUENCE: 5

Asn Val Thr Ser Ile His Ser Leu Leu Asp Glu Gly Lys Gln Ser
1               5                   10                  15

<210> SEQ ID NO 6
<211> LENGTH: 15
<212> TYPE: PRT
<213> ORGANISM: Mycobacterium tuberculosis

<400> SEQUENCE: 6

His Ser Leu Leu Asp Glu Gly Lys Gln Ser Leu Thr Lys Leu Ala
1               5                   10                  15

<210> SEQ ID NO 7
<211> LENGTH: 15
<212> TYPE: PRT
<213> ORGANISM: Mycobacterium tuberculosis

<400> SEQUENCE: 7

Glu Gly Lys Gln Ser Leu Thr Lys Leu Ala Ala Ala Trp Gly Gly
1               5                   10                  15

<210> SEQ ID NO 8
<211> LENGTH: 15
<212> TYPE: PRT
<213> ORGANISM: Mycobacterium tuberculosis

<400> SEQUENCE: 8

Leu Thr Lys Leu Ala Ala Ala Trp Gly Gly Ser Gly Ser Glu Ala
1               5                   10                  15

<210> SEQ ID NO 9
<211> LENGTH: 15
<212> TYPE: PRT
<213> ORGANISM: Mycobacterium tuberculosis
```

<400> SEQUENCE: 9

Ala Ala Trp Gly Gly Ser Gly Ser Glu Ala Tyr Gln Gly Val Gln
 1               5                  10                  15

<210> SEQ ID NO 10
<211> LENGTH: 15
<212> TYPE: PRT
<213> ORGANISM: Mycobacterium tuberculosis

<400> SEQUENCE: 10

Ser Gly Ser Glu Ala Tyr Gln Gly Val Gln Gln Lys Trp Asp Ala
 1               5                  10                  15

<210> SEQ ID NO 11
<211> LENGTH: 15
<212> TYPE: PRT
<213> ORGANISM: Mycobacterium tuberculosis

<400> SEQUENCE: 11

Tyr Gln Gly Val Gln Gln Lys Trp Asp Ala Thr Ala Thr Glu Leu
 1               5                  10                  15

<210> SEQ ID NO 12
<211> LENGTH: 15
<212> TYPE: PRT
<213> ORGANISM: Mycobacterium tuberculosis

<400> SEQUENCE: 12

Gln Lys Trp Asp Ala Thr Ala Thr Glu Leu Asn Asn Ala Leu Gln
 1               5                  10                  15

<210> SEQ ID NO 13
<211> LENGTH: 15
<212> TYPE: PRT
<213> ORGANISM: Mycobacterium tuberculosis

<400> SEQUENCE: 13

Thr Ala Thr Glu Leu Asn Asn Ala Leu Gln Asn Leu Ala Arg Thr
 1               5                  10                  15

<210> SEQ ID NO 14
<211> LENGTH: 15
<212> TYPE: PRT
<213> ORGANISM: Mycobacterium tuberculosis

<400> SEQUENCE: 14

Asn Asn Ala Leu Gln Asn Leu Ala Arg Thr Ile Ser Glu Ala Gly
 1               5                  10                  15

<210> SEQ ID NO 15
<211> LENGTH: 15
<212> TYPE: PRT
<213> ORGANISM: Mycobacterium tuberculosis

<400> SEQUENCE: 15

Asn Leu Ala Arg Thr Ile Ser Glu Ala Gly Gln Ala Met Ala Ser
 1               5                  10                  15

<210> SEQ ID NO 16
<211> LENGTH: 15
<212> TYPE: PRT
<213> ORGANISM: Mycobacterium tuberculosis

<400> SEQUENCE: 16

Ile Ser Glu Ala Gly Gln Ala Met Ala Ser Thr Glu Gly Asn Val
1               5                   10                  15

<210> SEQ ID NO 17
<211> LENGTH: 15
<212> TYPE: PRT
<213> ORGANISM: Mycobacterium tuberculosis

<400> SEQUENCE: 17

Gln Ala Met Ala Ser Thr Glu Gly Asn Val Thr Gly Met Phe Ala
1               5                   10                  15

<210> SEQ ID NO 18
<211> LENGTH: 15
<212> TYPE: PRT
<213> ORGANISM: Mycobacterium tuberculosis

<400> SEQUENCE: 18

Met Ala Glu Met Lys Thr Asp Ala Ala Thr Leu Ala Gln Glu Ala
1               5                   10                  15

<210> SEQ ID NO 19
<211> LENGTH: 15
<212> TYPE: PRT
<213> ORGANISM: Mycobacterium tuberculosis

<400> SEQUENCE: 19

Thr Asp Ala Ala Thr Leu Ala Gln Glu Ala Gly Asn Phe Glu Arg
1               5                   10                  15

<210> SEQ ID NO 20
<211> LENGTH: 15
<212> TYPE: PRT
<213> ORGANISM: Mycobacterium tuberculosis

<400> SEQUENCE: 20

Leu Ala Gln Glu Ala Gly Asn Phe Glu Arg Ile Ser Gly Asp Leu
1               5                   10                  15

<210> SEQ ID NO 21
<211> LENGTH: 15
<212> TYPE: PRT
<213> ORGANISM: Mycobacterium tuberculosis

<400> SEQUENCE: 21

Gly Asn Phe Glu Arg Ile Ser Gly Asp Leu Lys Thr Gln Ile Asp
1               5                   10                  15

<210> SEQ ID NO 22
<211> LENGTH: 15
<212> TYPE: PRT
<213> ORGANISM: Mycobacterium tuberculosis

<400> SEQUENCE: 22

Ile Ser Gly Asp Leu Lys Thr Gln Ile Asp Gln Val Glu Ser Thr
1               5                   10                  15

<210> SEQ ID NO 23
<211> LENGTH: 15
<212> TYPE: PRT
<213> ORGANISM: Mycobacterium tuberculosis

<400> SEQUENCE: 23

Lys Thr Gln Ile Asp Gln Val Glu Ser Thr Ala Gly Ser Leu Gln

-continued

```
1               5                   10                  15
```

<210> SEQ ID NO 24
<211> LENGTH: 15
<212> TYPE: PRT
<213> ORGANISM: Mycobacterium tuberculosis

<400> SEQUENCE: 24

```
Gln Val Glu Ser Thr Ala Gly Ser Leu Gln Gly Gln Trp Arg Gly
1               5                   10                  15
```

<210> SEQ ID NO 25
<211> LENGTH: 15
<212> TYPE: PRT
<213> ORGANISM: Mycobacterium tuberculosis

<400> SEQUENCE: 25

```
Ala Gly Ser Leu Gln Gly Gln Trp Arg Gly Ala Ala Gly Thr Ala
1               5                   10                  15
```

<210> SEQ ID NO 26
<211> LENGTH: 15
<212> TYPE: PRT
<213> ORGANISM: Mycobacterium tuberculosis

<400> SEQUENCE: 26

```
Gly Gln Trp Arg Gly Ala Ala Gly Thr Ala Ala Gln Ala Ala Val
1               5                   10                  15
```

<210> SEQ ID NO 27
<211> LENGTH: 15
<212> TYPE: PRT
<213> ORGANISM: Mycobacterium tuberculosis

<400> SEQUENCE: 27

```
Ala Ala Gly Thr Ala Ala Gln Ala Ala Val Val Arg Phe Gln Glu
1               5                   10                  15
```

<210> SEQ ID NO 28
<211> LENGTH: 15
<212> TYPE: PRT
<213> ORGANISM: Mycobacterium tuberculosis

<400> SEQUENCE: 28

```
Ala Gln Ala Ala Val Val Arg Phe Gln Glu Ala Ala Asn Lys Gln
1               5                   10                  15
```

<210> SEQ ID NO 29
<211> LENGTH: 15
<212> TYPE: PRT
<213> ORGANISM: Mycobacterium tuberculosis

<400> SEQUENCE: 29

```
Val Arg Phe Gln Glu Ala Ala Asn Lys Gln Lys Gln Glu Leu Asp
1               5                   10                  15
```

<210> SEQ ID NO 30
<211> LENGTH: 15
<212> TYPE: PRT
<213> ORGANISM: Mycobacterium tuberculosis

<400> SEQUENCE: 30

```
Ala Ala Asn Lys Gln Lys Gln Glu Leu Asp Glu Ile Ser Thr Asn
1               5                   10                  15
```

```
<210> SEQ ID NO 31
<211> LENGTH: 15
<212> TYPE: PRT
<213> ORGANISM: Mycobacterium tuberculosis

<400> SEQUENCE: 31

Lys Gln Glu Leu Asp Glu Ile Ser Thr Asn Ile Arg Gln Ala Gly
1               5                   10                  15

<210> SEQ ID NO 32
<211> LENGTH: 15
<212> TYPE: PRT
<213> ORGANISM: Mycobacterium tuberculosis

<400> SEQUENCE: 32

Glu Ile Ser Thr Asn Ile Arg Gln Ala Gly Val Gln Tyr Ser Arg
1               5                   10                  15

<210> SEQ ID NO 33
<211> LENGTH: 15
<212> TYPE: PRT
<213> ORGANISM: Mycobacterium tuberculosis

<400> SEQUENCE: 33

Ile Arg Gln Ala Gly Val Gln Tyr Ser Arg Ala Asp Glu Glu Gln
1               5                   10                  15

<210> SEQ ID NO 34
<211> LENGTH: 15
<212> TYPE: PRT
<213> ORGANISM: Mycobacterium tuberculosis

<400> SEQUENCE: 34

Val Gln Tyr Ser Arg Ala Asp Glu Glu Gln Gln Gln Ala Leu Ser
1               5                   10                  15

<210> SEQ ID NO 35
<211> LENGTH: 15
<212> TYPE: PRT
<213> ORGANISM: Mycobacterium tuberculosis

<400> SEQUENCE: 35

Ala Asp Glu Glu Gln Gln Gln Ala Leu Ser Ser Gln Met Gly Phe
1               5                   10                  15

<210> SEQ ID NO 36
<211> LENGTH: 95
<212> TYPE: PRT
<213> ORGANISM: Mycobacterium tuberculosis

<400> SEQUENCE: 36

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
```

```
<210> SEQ ID NO 37
<211> LENGTH: 100
<212> TYPE: PRT
<213> ORGANISM: Mycobacterium tuberculosis

<400> SEQUENCE: 37

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
            85                  90                  95

Gln Met Gly Phe
            100
```

DIAGNOSTICS METHOD

This application is a national phase under 35 U.S.C. 371 Int'l Patent Appln. No. PCT/GB2003/002936 filed Jul. 7, 2003.

FIELD OF THE INVENTION

The invention relates to a method of diagnosing the infection status of individuals.

BACKGROUND OF THE INVENTION

Infection by a pathogen may or may not cause disease symptoms in an individual. Although therapeutic products are available for treating infection by pathogens, prolonged use of these products may be harmful. Therefore it is desirable to target use of the therapeutic products to individuals who are more likely to develop disease symptoms. Targeting therapy in this way will also be more cost-effective.

SUMMARY OF THE INVENTION

Long term infected individuals who have not developed disease symptoms are much less likely to develop disease symptoms than recently exposed individuals. For example following exposure to *M. tuberculosis* individuals have a risk of approximately 10% of progressing to active tuberculosis with disease symptoms in the first one to two years following exposure. If active tuberculosis does not manifest within the first one to two years then the residual risk of progress to active tuberculosis is 5% over the remaining lifetime of the individual. It is therefore desirable to target recently infected individuals for preventative treatment because they have a high probability of progressing to disease.

Some groups of individuals have a higher risk for developing active tuberculosis, such as young children (less than 5 years old), newborn babies (less than 1 year old), individuals with HIV infection or on immunosuppressive medication such as corticosteroids (typically oral corticosteroids), such as prednisolone, or antibodies against TNF-∀ (typically monoclonal and/or humanised), such as infliximab. It is even more important to diagnose recent exposure to pathogen in such individuals.

The inventors have found that T cells from individuals recently exposed to an intracellular pathogen react to whole proteins from the pathogen but do not react to, or show substantially less reaction to, peptide epitopes from the pathogen. It is believed that this may be because when a cellular T cell immune response has just been primed (induced) by a recent infection the T cells are of a lower affinity for their cognate ligand, as fine-tuning of the epitope specificity and clonal expansion of the different T cell populations is still going on. Since in T cell response assays whole protein is presented to T cells after uptake and processing by antigen presenting cells (APCs) followed by presentation of the optimal peptide epitopes in the context of MHC molecules at the APC surface, even cells of relatively low affinity will recognise these optimum naturally processed and presented epitopes.

In contrast short multiple peptide epitopes from the pathogen even when they together represent the entire sequence of a protein antigen are not normally the optimal epitopes, but merely tend to contain the optimum epitope sequence within their sequence. Therefore recognition of these peptides will require T cells to be present which are of higher affinity to the optimal epitope. It is believed that such T cells only appear in the later course of infection, when the T cell repertoire is more mature and focussed, and would not be present in recently exposed individuals.

Accordingly the invention provides a method of diagnosing in an individual recent exposure to an agent which is a pathogen, a vaccine or a moiety which causes a cellular immune response, said method comprising determining in vitro or in vivo whether the T cells of the individual recognise a protein from said agent having a length of at least 30 amino acids to a greater extent than a peptide epitope from the agent, a greater extent of recognition of the protein indicating that the individual has recently been exposed to the agent.

Preferably in the method the pathogen is *M. tuberculosis* and the peptide epitope and/or protein is from ESAT-6 or CFP10.

The inventors have also shown using a T cell detection (ex vivo ELISPOT) based technique that T cells from the individuals exposed to a pathogen reacted to antigen from the pathogen at 3 months from exposure, but no longer reacted to antigen at 6 months from exposure. Given that the presence of effector T cells indicates the presence of infection by a pathogen this shows these individuals had cleared the infection which had been detected initially. This elucidation of the dynamics of the T cell response during infection and clearance of infection shows the need to test at a subsequent time point to avoid treating individuals who naturally clear infection.

Accordingly the invention provides a method of diagnosing an individual who has cleared an infection by a pathogen comprising determining whether the T cells of the individual recognise antigen from the pathogen at a first and a subsequent second time point after exposure to the pathogen, wherein the finding that the T cells recognise antigen at the first time point and not at the second time point indicates that the individual has cleared the infection.

In addition the inventors have identified individuals whose T cells did not react at 3 months from exposure but did react at 6 months from exposure. These individuals are mounting a slower weaker response to infection. They are therefore less likely to be able to control the infection and are more likely to progress to active disease. It is therefore desirable to target this group of individuals for treatment.

Accordingly the invention provides a method of diagnosing an individual who is more likely to progress to active disease after exposure to a pathogen comprising determining whether the T cells of the individual recognise antigen from the pathogen at a first and subsequent second time point after exposure to the pathogen, wherein the finding that the T cells do not recognise the antigen at the first time point, but do recognise the antigen at the second time point indicates that the individual is more likely to progress to active disease.

The finding may also be used in a method of diagnosing an individual who mounts a weaker response to a vaccine or a moiety which induces a cellular response after exposure to the vaccine or moiety comprising determining whether the T cells of the individual recognise antigen from the vaccine or moiety at a first and subsequent second time point after exposure, wherein the finding that the T cells do not recognise the antigen at the first time point, but do recognise the antigen at the second time point indicates that the individual is mounting a weaker response to the vaccine or moiety.

The inventors have also shown advantages in detection of latent mycobacterial infection by using the T cell detection assays described herein in individuals on immunosuppressive therapy or about to start immunosuppressive therapy.

Accordingly the invention provides a method of diagnosing susceptibility to active tuberculosis disease and latent mycobacterial infection in an individual on or about to start immunosuppressive therapy comprising detecting whether or not the T cells of the individual recognise mycobacterial antigen, wherein recognition of mycobacterial antigen by the T cells indicates susceptibility to active tuberculosis disease and latent mycobacterial infection.

In addition the invention provides a method of monitoring susceptibility to active tuberculosis disease and latent mycobacterial infection in an individual on immunosuppressive therapy comprising detecting whether or not the T cells of the individual recognise mycobacterial antigen, wherein recognition of mycobacterial antigen by the T cells indicates susceptibility to active tuberculosis disease and latent mycobacterial infection.

The inventors have shown that effector T cells specific for mycobacterial antigen increase markedly prior to the onset of active symptomatic mycobacterial infection. Thus detection of this increase in effector T cells may be used as a predictor of progression, or susceptibility to progression to disease in asymptomatic latently infected individuals.

Accordingly the invention provides a method of detecting susceptibility to onset of active mycobacterial disease in an individual who does not have any symptoms of mycobacterial disease comprising determining whether the individual has increased levels of T cells which recognise a mycobacterial antigen, to thereby determine whether the individual is susceptible to onset of active mycobacterial disease. This would allow doctors to initiate radiological and other investigations in asymptomatic individuals with latent mycobacterial infection, and to diagnose and treat early active disease before the onset of symptoms. Such early treatment, even before symptoms have begun, would prevent considerable morbidity and mortality, especially for (but not limited to) people with multi-drug resistant tuberculosis.

DETAILED DESCRIPTION OF THE INVENTION

Different aspects of the invention are discussed below. It is to be understood that the specific T cell detection techniques which are discussed below in the context of one aspect of the invention (particularly the method of diagnosing recent exposure) may be used in other aspects of the invention. Thus the description of the types and numbers of peptide epitopes/ proteins (including their length, origin, sequence and analogues) used in the detection method, the manner in which the reaction of the T cell is detected (including change of state), the types of T cell samples which are used, the way such samples may be processed, the form of the T cells in the assay and the specific manner in which the T cell detection is carried out, that is given for the method of diagnosing recent exposure is also relevant to the other aspects of the invention.

Similarly, the types of individuals to be tested and the types of mycobacterium with which individuals may be infected discussed in the context of the method of diagnosing recent exposure is applicable to the other aspects of the invention.

Method of Diagnosing Recent Exposure

The method of the invention comprises determining whether the T cells of an individual recognise a protein (with a length of at least 30 amino acids) from an agent to a greater extent than a peptide epitope from the agent. This may be done by detecting the reaction of the T cells either to the protein and peptide epitope or to an analogue of either of these (discussed below). It is understood that herein reference to "protein" or "peptide epitope" from the pathogen will also include the analogues of these molecules unless the context requires otherwise.

The method is generally performed on a sample from an individual who is preferably a human, but may be an animal (typically an animal which can be naturally or artificially infected by the relevant pathogen). Thus the individual may be a mammal, such as a primate, cow, sheep, pig, badger or rodent, e.g. a mouse or rat. The individual may be at risk of (natural) exposure to the pathogen, for example the individual may live in an area in which the pathogen occurs. The individual may have an increased risk of becoming infected, typically for socio-economic reasons or may have a genetic or acquired predisposition to the pathogen. In one embodiment the exposure is not a natural exposure (i.e. it is an artificial exposure), for example intentional exposure of an animal model to a pathogen. In another embodiment the exposure is to a non-natural (typically intentional) release of the pathogen in the area where the host (including humans) lives.

The pathogen may be an extracellular pathogen, but is preferably an intracellular pathogen, and is generally a naturally occurring pathogen (not modified artificially). The pathogen is typically able to infect any of the specific species of host mentioned herein. It may be a virus, bacterium or fungus, such as HPV, HIV, HCV, a *Chlamydia* species, HBV, EBV, CMV, VZV, HSV, *Legionella, S. typhi, P. falciparum, Leishmaniasis, M. leprae*, influenza virus, foot and mouth virus, a *Toxoplasma* species, a *Brucella* species, a *Cryptococcus* species, a *Candida* species or an *Aspergillus* species.

In a preferred embodiment the pathogen is a mycobacterium. The mycobacterium typically expresses ESAT-6 or CFP10, and may be *M.tuberculosis*. The mycobacterium may be *M.marinum* or *M.kansasii*. The pattern of clinical symptoms can be used to distinguish between these two organisms and *M.tuberculosis*. The mycobacterium may be *M. bovis* (which infects cows, but can also infect humans and other species such as badgers and monkeys).

In the case where the agent is a vaccine the vaccine may contain antigen from (provide protection against) any of the pathogens mentioned herein. Any of the types of agent mentioned herein may be capable of inducing a cellular response in the individual, typically a T cell and/or NK cell response.

The protein and/or peptide epitope of the pathogen may be of any of the pathogens mentioned herein, preferably being mycobacterial. In one embodiment the protein is, or contains sequence from, a particular pathogen protein, whilst the peptide epitope is from a different protein from the pathogen. However preferably the peptide epitope is an epitope within the protein, i.e. the protein comprises the sequence of the peptide epitope. The peptide epitope generally contains within its sequence an optimal epitope, typically flanked by one or more amino acids at the N or C terminal end of the optimal epitope sequence.

The protein may be a membrane protein, a cytoplasmic protein (present in the cytoplasm of the pathogen or a cell which it has infected), a secreted protein (secreted from the pathogen and/or from the infected cell), an enzyme, a structural protein or a regulatory protein. The protein may be one which typically comprises at least 10%, such as at least 30% or 50% of the dry mass of the agent. The protein may be one which in its natural form and/or as used in the method comprises at least 5, such as at least 10 or 15 CD4 and/or CD8 T cell epitopes.

The peptide epitope is typically a fragment of any of the pathogen proteins mentioned. In the case of *M. tuberculosis* the peptide epitope may be any of the peptides shown below from ESAT-6 (SEQ ID NO: 36) and CFP-10 (SEQ ID NO: 37).

Peptides from ESAT-6 (SEQ ID NOS: 1-17, respectively):

```
MTEQQWNFAGIEAAA      (SEQ. ID NO: 1)
WNFAGIEAAASAIQG      (SEQ. ID NO: 2)
IEAAASAIQGNVTSI      (SEQ. ID NO: 3)
SAIQGNVTSIHSLLD      (SEQ. ID NO: 4)
NVTSIHSLLDEGKQS      (SEQ. ID NO: 5)
HSLLDEGKQSLTKLA      (SEQ. ID NO: 6)
EGKQSLTKLAAAWGG      (SEQ. ID NO: 7)
LTKLAAAWGGSGSEA      (SEQ. ID NO: 8)
AAWGGSGSEAYQGVQ      (SEQ. ID NO: 9)
SGSEAYQGVQQKWDA      (SEQ. ID NO: 10)
YQGVQQKWDATATEL      (SEQ. ID NO: 11)
QKWDATATELNNALQ      (SEQ. ID NO: 12)
TATELNNALQNLART      (SEQ. ID NO: 13)
NNALQNLARTISEAG      (SEQ. ID NO: 14)
NLARTISEAGQAMAS      (SEQ. ID NO: 15)
ISEAGQAMASTEGNV      (SEQ. ID NO: 16)
QAMASTEGNVTGMFA      (SEQ. ID NO: 17)
```

Peptides from CFP-10 (SEQ ID NOS: 18-35, respectively):

```
MAEMKTDAATLAQEA      (SEQ ID NO: 18)
TDAATLAQEAGNFER      (SEQ ID NO: 19)
LAQEAGNFERISGDL      (SEQ ID NO: 20)
GNFERISGDLKTQID      (SEQ ID NO: 21)
ISGDLKTQIDQVEST      (SEQ ID NO: 22)
KTQIDQVESTAGSLQ      (SEQ ID NO: 23)
QVESTAGSLQGQWRG      (SEQ ID NO: 24)
AGSLQGQWRGAAGTA      (SEQ ID NO: 25)
GQWRGAAGTAAQAAV      (SEQ ID NO: 26)
AAGTAAQAAVVRFQE      (SEQ ID NO: 27)
AQAAVVRFQEAANKQ      (SEQ ID NO: 28)
VRFQEAANKQKQELD      (SEQ ID NO: 29)
AANKQKQELDEISTN      (SEQ ID NO: 30)
KQELDEISTNIRQAG      (SEQ ID NO: 31)
EISTNIRQAGVQYSR      (SEQ ID NO: 32)
IRQAGVQYSRADEEQ      (SEQ ID NO: 33)
VQYSRADEEQQQALS      (SEQ ID NO: 34)
ADEEQQQALSSQMGF      (SEQ ID NO: 35)
```

The peptide epitope typically has a length of at least 8 to 29 amino acids, such as 12 to 25 amino acids. The protein typically has a length of at least 30 to 400 amino acids, such as 50 to 300, or 80 to 200 amino acids in length. The protein may be the same as the whole naturally occurring protein, or a fragment thereof. In one embodiment it is in the form of a fusion protein, for example with non-pathogen protein sequence. Generally the protein comprises a pathogen sequence (sequence from a protein of the pathogen) which is at least 8, for example at least 12, 18, 25 or 30 amino acids long.

The method of the invention may be performed using any suitable technique. Different techniques are discussed below and include techniques which detect the reaction of T cells or which quantitate antigen specific T cells. These techniques may be based on detection of 'spots' of a substance secreted from T cells (such as ELISPOT), sorting (counting) of T cells (for example using intracellular staining or FACS), use of MHC tetramers (for example in a sorting technique) or an ELISA technique.

The method of the invention is generally based on the detection of different levels of response from and/or different frequencies of T cells in an individual to one or more proteins and one or more (smaller) peptide epitopes from a pathogen. The T cells which react are specific for/bind to amino acid sequence in the protein or peptide epitope. The T cells which are analysed in the method may be CD4 and/or CD8 T cells, (* T cells or CD1 restricted T cells. The T cells have been pre-sensitised in vivo to protein from the pathogen.

The method of the invention may be performed using a technique which detects T cell reaction to a protein/peptide epitope. In many such techniques whether or not the T cells of the individual react to the protein or peptide epitope will be readily apparent, and thus individuals will be diagnosed as having been recently exposed if their T cells react to the protein and do not react to the peptide epitope. Suitable thresholds may be determined by the skilled persons. In one embodiment arbitrary thresholds are used to determine positive and negative responses.

Typically the method will be performed in a manner in which reactive T cells present at a frequency of at least about 20 per million peripheral blood mononuclear cells (PBMCs) will be detectable (a positive result), and preferably distinguishable from a reactive T cells present at a frequency of about 19 per million PBMCs or less (a negative result).

Thus individuals will typically be selected as being exposed recently to pathogen if they are found to have T cells which are able to recognise the protein at a frequency of at least 20 per million PBMCs and if they are found to have less than 19 per million PBMCs which recognise the peptide epitope. It is understood though that a positive and negative result may be defined using thresholds different from these specific thresholds.

In a preferred embodiment the T cells are detected by:
(i) contacting in vitro or in vivo a first population of T cells from the individual with one or more peptide epitopes from the pathogen (including an analogue of said peptide which is recognised by T cells that recognise said peptide), and determining the reaction of the T cells to the peptide epitope(s), and (ii) contacting in vitro or in vivo a second population of T cells from the individual with a protein from the pathogen (including an analogue of said protein which is recognised by T cells that recognise said protein), wherein the protein has a length of at least 30 amino acids and determining the reaction of the T cells to the protein.

Determination of whether the T cells react to/recognise the protein or peptide epitope is may be done by detecting a change in the state of the T cells in the presence of the protein or peptide epitope. The change in state is generally caused by antigen specific functional activity of the T cell after the T cell receptor binds the protein (after it is processed) or peptide epitope. Generally when binding the T cell receptor the processed protein or peptide is bound to an MHC class I or II molecule, which is typically present on the surface of an antigen presenting cell (APC).

The change in state of the T cell may be the start of or increase in secretion of a substance from the T cell, such as a cytokine, especially IFN-(, IL-2 or TNF-∀. Determination of IFN-( secretion is particularly preferred. In one embodiment more than one cytokine is detected, such as 2, 3, 4 to 10 or more cytokines. Intracellular changes may be detected, for example by using intracellular staining techniques, typically intracellular cytokine staining (e.g. for any of the cytokines mentioned herein). The staining can be detected using a cell sorting technique, for example using a FACS technique.

The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilised on a solid support. The support may be a well (typically in an assay plate) or may be a microsphere. In one embodiment this allows the actual number of responding T cells to be determined since after binding the agent the substance will remain in the vicinity of the T cell which secreted it. Thus 'spots' of substance/agent complex may form on the support, each spot representing a T cell which is secreting the substance. Quantifying the spots (and typically comparing against a control) allows determination of recognition of the peptide.

After the substance is allowed to bind, the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-( secreted from the T cell is bound by a first IFN-( specific antibody which is immobilised on a solid support. The bound IFN-( is then detected using a second IFN-( specific antibody which is labelled with a detectable label. Other detectable labels may be used.

In another embodiment detection is performed using a multiplex analysis of cytokines performed using microspheres coated with antibody specific to a cytokine. Detection antibodies (that bind to the cytokine bound to the antibody on the microsphere) are may be used. Such detection antibodies may be labelled, for example with a fluorescent label. The detection technique may be based on the Luminex multiplex cytokine detection system.

Typically the T cells used in the method are taken from the individual in a blood sample, although other types of body sample which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present peptide to the T cells. In another embodiment only T cells, such as only CD4 T cells, can be purified from the sample. PBMCs, MCs and T cells can be separated from the sample using techniques known in the art, such as those described in Lalvani et al (1997) *J.Exp. Med.* 186, p859-865.

In the case of a blood sample, red blood cells may be removed from the sample (to leave serum and other cells).

In one embodiment the T cells which are detected are in the form of unprocessed or diluted samples. The T cells are preferably directly ex vivo, i.e. they are not cultured before being used in the method. The T cells are typically freshly isolated T cells (such as in the form of freshly isolated MCs or PBMCs).

The APC which is typically present in the method may be from the same individual as the T cell or from a different individual. The APC may be a naturally occurring APC or an artificial APC. The APC is a cell which is capable of presenting peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class I or II molecules on its surface.

In one embodiment of the method more than one protein from the pathogen (typically at least 2, 5, 10 or more different proteins) and/or more than one peptide epitope from the pathogen (typically at least 2, 5, 10 or more different peptide epitopes) may be used. Thus, for example, the T cells can be placed into an assay with all the proteins or peptide epitopes (i.e. a pool of the proteins or peptides) which it is intended to test. Alternatively the T cells can be divided and placed into separate assays each of which contain one or some of the proteins or peptides which it is intended to test.

In one embodiment the protein or peptide epitope is provided to the APC in the absence of the T cell. The APC is then provided to the T cell, typically after being allowed to present the processed protein or peptide epitope on its surface. Presented peptide may have been taken up inside the APC and presented, or simply be taken up onto the surface without entering inside the APC.

The duration for which the protein or peptide epitope is contacted with the T cells will vary depending on the method used for determining recognition. Typically $10^4$ to $10^7$, preferably $1\times10^5$ to $5\times10^5$ PBMCs are added to each assay. The peptide is typically used in the assay at a concentration of from $10^{-1}$ to $10^3$ µg/ml, preferably 0.5 to 50 µg/ml or 1 to 10 µg/ml.

Typically the length of time for which the T cells are incubated with the protein or peptide is from 4 to 72 hours, preferably 6 to 48, 8 to 24 or 10 to 16 hours. When using ex vivo PBMCs it has been found that $0.3\times10^6$ PBMCs can be incubated in 10 µg/ml of peptide for 12 hours at 37° C.

The method may be based on an ELISA method, such as the whole blood Quantiferon system (for example as available from Cellestis).

In one embodiment instead of the protein and/or peptide epitope analogues are used which are recognised by T cells which recognise the protein or peptide. Thus such analogues may be identified by routine means and their ability to be recognised by the relevant T cells can be tested using any suitable technique mentioned herein. For the proteins such recognition will of course be after processing and presentation of the protein and/or analogue by an APC.

The analogue will generally have similar binding properties to the protein and/or peptide and thus typically binds to the same MHC molecule. The analogue may bind to antibodies specific for the protein or peptide, and thus may inhibit binding of the protein or peptide to such an antibody.

The analogue is typically a protein or peptide. It may have homology with the equivalent original protein or peptide. A peptide which is homologous to another peptide is typically at least 70% homologous to the peptide, preferably at least 80 or 90% and more preferably at least 95%, 97% or 99% homologous thereto, for example over a region of at least 8, preferably at least 15, for instance at least 40, 60 or 100 or more contiguous amino acids. The analogue typically differs from the protein or peptide by 1, 2, less than 6, such as less than 12 mutations (each of which is a substitution (e.g. a conservative substitution), deletion or insertion) for example over any of the above-mentioned lengths of region mentioned for homology.

Methods of measuring protein homology are well known in the art and it will be understood by those of skill in the art that in the present context, homology is calculated on the basis of amino acid identity (sometimes referred to as "hard homology"). For example the UWGCG Package provides the BESTFIT program which can be used to calculate homology (for example used on its default settings) (Devereux et al (1984) *Nucleic Acids Research* 12, p387-395).

An analogue which is a protein or peptide typically has any of the amino acid lengths mentioned above for the protein or peptide discussed above and/or may be part of a fusion protein. Typically the amino acids in the analogue at the equivalent positions to amino acids in the original protein or peptide which contribute to binding the MHC molecule or are responsible for the recognition by the T cell receptor, are the same or are conservative changes.

Conservative substitutions are defined in the table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Typically the analogue of the protein or peptide comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The analogues may comprise one or more non-natural amino acids, for example amino acids with a side chain different from natural amino acids. Generally, the non-natural amino acid will have an N terminus and/or a C terminus. The non-natural amino acid may be an L- or D-amino acid. The analogues typically has a shape, size, flexibility or electronic configuration which is substantially similar to the original protein or peptide. It is typically a derivative of the original protein or peptide.

The analogue is typically designed by computational means and then synthesised using methods known in the art. Alternatively the analogue can be selected from a library of compounds. The library may be a combinatorial library or a display library, such as a phage display library. The library of compounds may be expressed in the display library in the form of being bound to a MHC class I or II molecule, such as the MHC molecule which the original peptide binds. Analogues are generally selected from the library based on their ability to mimic the binding characteristics of the original protein or peptide. Thus they may be selected based on ability to bind a T cell receptor or antibody which recognises the original protein or peptide.

In one embodiment the T cells are detected not based on their response to a substance but based on their ability to bind a specific binding agent. Typically the agent is or comprises any of the proteins, peptide epitopes or analogues mentioned herein. The agent may be labelled (for example using any of the detectable labels mentioned herein). The specific binding agent may comprise an MHC molecule, and is preferably an MHC tetramer-peptide complex.

The peptide or analogue discussed herein can be made using standard synthetic chemistry techniques, such as by use of an automated synthesizer. They can be made from a longer polypeptide, e.g. a fusion protein, which polypeptide typically comprises the sequence of the peptide, and may be derived from the polypeptide by for example hydrolysing the polypeptide, such as using a protease; or by physically breaking the polypeptide. The protein may be expressed recombinantly.

In the case where the method is performed in vivo the protein, peptide epitope and/or analogue may be administered by any suitable means and at any suitable dose, for example in the form, by the route or at the dosage discussed for the therapeutic product below. Administration to the skin is preferred.

The invention also provides a method of treating an individual comprising administering to an individual diagnosed as having been recently exposed to a pathogen by the diagnosis method a product which prevent or treats the condition caused by the pathogen. Thus the invention provides use of the product in the manufacture of a medicament for the treatment of an individual who has been diagnosed as having been recently exposed to the pathogen by a method of the invention. Typically a non-toxic effective amount of the therapeutic agent is administered.

In the case *M. tuberculosis* the therapeutic agent may be rifampicin, isoniazid, pyrazinamide, ethambutol, streptomycin, para-amino-salicyclic acid, kanamyin, capreomycin, ethionamide, cycloserine, thiacetazone or a flouroquinolone (e.g. ciprofloxacin).

The product may be in the form of a pharmaceutical composition which comprises the agent and a pharmaceutically acceptable carrier or diluent. Suitable carriers and diluents include isotonic saline solutions, for example phosphate-buffered saline. Typically the product is administered by parenteral, intravenous, intramuscular, subcutaneous, transdermal, intradermal, oral, intranasal, inhalation (into the lungs), intravaginal, or intrarectal administration.

The dose of the product may be determined according to various parameters, especially according to the particular agent; the age, weight and condition of the patient to be treated; the route of administration; and the required regimen.

A physician will be able to determine the required route of administration and dosage for any particular patient. A suitable dose may however be from 10 μg to 10 g, for example from 100 μg to 1 g of the product.

Methods of Diagnosis or Testing of Vaccines Comprising Testing at Two Time Points The inventors have also shown using a T cell detection (ex vivo ELISPOT) based technique that T cells from the individuals exposed to a pathogen reacted to antigen from the pathogen at 3 months from exposure, but no longer reacted to antigen at 6 months from exposure. Given that the presence of effector T cells indicates the presence of infection by a pathogen this shows these individuals had cleared the infection which had been detected initially. This elucidation of the the dynamics of the T cell response during infection and clearance of infection shows the need to test at a subsequent time point to avoid treating individuals who naturally clear infection.

Accordingly the invention provides a method of diagnosing an individual who has cleared an infection by a pathogen comprising determining whether the T cells of the individual recognise antigen from the pathogen at a first and a subsequent second time point after exposure to the pathogen, wherein the finding that the T cells recognise antigen at the first time point and not at the second time point indicates that the individual has cleared the infection.

The infection may be cleared naturally by the immune response of the individual but could also be cleared pharmacologically by use of a product which treats the infection.

In addition the inventors have identified individuals whose T cells did not react at 3 months from exposure but did react at 6 months from exposure. These individuals are mounting a slower weaker response to infection. They are therefore less likely to be able to control the infection and are more likely to progress to active disease. It is therefore desirable to target this group of individuals for treatment.

Accordingly the invention provides a method of diagnosing an individual who is more likely to progress to active disease after exposure to a pathogen comprising determining whether the T cells of the individual recognise antigen from the pathogen at a first and subsequent second time point after exposure to the pathogen, wherein the finding that the T cells do not recognise the antigen at the first time point, but do recognise the antigen at the second time point indicates that the individual is more likely to progress to active disease.

The finding may also be used in a method of diagnosing an individual who mounts a weaker response to a vaccine or a moiety which induces a cellular response after exposure to the vaccine or moiety comprising determining whether the T cells of the individual recognise antigen from the vaccine or moiety at a first and subsequent second time point after exposure, wherein the finding that the T cells do not recognise the antigen at the first time point, but do recognise the antigen at the second time point indicates that the individual is mounting a weaker response to the vaccine or moiety.

Further testing at a subsequent time point may also be used to test the efficacy of a vaccine. Accordingly the invention provides a method of testing the efficacy of a vaccine which has been administered to an individual comprising determining whether the T cells of the individual recognise antigen from the pathogen at a first and a subsequent second time point after exposure to the pathogen, wherein the finding that the T cells recognise antigen at the first time point and not at the second time point indicates that the vaccine antigen has been cleared and is not persisting.

If the vaccine is found to have low efficacy (i.e. is being cleared) then the individual may need to receive an additional or augmented dose of the vaccine or be vaccinated with an alternative vaccine. Thus the same vaccine may be administered to the individual again optionally at increased dose. Alternatively a different vaccine may be administered (for example containing different antigens/proteins).

In the above methods the first time point and second time point are typically separated by about 2 to 16 weeks, such as about 4 to 12 weeks. The first time point may be about 8 to 16 weeks (preferably about 12 weeks) after exposure and/or the second time point may be about 18 to 48 weeks (preferably about 24 weeks) after exposure.

The individuals who are diagnosed may be any of the individuals who are mentioned herein, but are preferably human. The said determining of T cell recognition may be carried out using any suitable method, such as any suitable method disclosed herein. The antigen may be any antigen which is recognised by T cells (such as any type of T cell mentioned herein) and thus may be any of the proteins or peptide epitopes mentioned herein. Analogues of the antigen may be used in the determination such as any of the types of, or specific, analogues mentioned herein Typically the pathogen is an intracellular pathogen such as any such pathogen mentioned herein, for example HPV, HIV, SIV, HCV, a *Chlamydia* species, HBV, EBV, CMV, VZV, HSV, *Legionella, S. typhi, P. falciparum, Leishmaniasis, M. leprae,* influenza virus, foot and mouth virus, a *Toxoplasma* species, a *Brucella* species, a *Cryptococcus* species, a *Candida* species or an *Aspergillus* species. Preferably the pathogen is *M. tuberculosis.*

As mentioned above the recognition of the antigen or analogue may be determined using any suitable method, but is preferably determined by detecting secretion of a cytokine from the T cells, such as IFN-(.

The above method which involves determining T cell recognition at two time points may be used to diagnose individuals who have a high probability of progressing to active disease. The invention provides a method of treating an individual who has been diagnosed in this way comprising administering to the individual a product which prevent or treats the condition caused by the pathogen.

Preferably the pathogen is *M. tuberculosis* and/or the agent is rifampicin, isoniazid, pyrazinamide, ethambutol, streptomycin, para-amino-salicyclic acid, kanamyin, capreomycin, ethionamide, cycloserine, thiacetazone or a flouroquinolone, or an analogue of such an agent.

The inventors also identified individuals who only tested positive with whole mycobacterial antigen and were negative with peptide, who were then negative (for antigen and peptide) at a subsequent time point. Thus a T cell response to antigen only predicts that the individual will clear infection. This shows that it is advantageous to combine the first aspect of the invention (testing with protein and peptide) and the second aspect of the invention (testing at two time points) to identify individuals who are recently exposed but have cleared infection.

Thus in one embodiment the invention provides a method of diagnosing an individual who has been recently exposed to a mycobacterium and is likely to have cleared the infection caused by the mycobacterium, said method comprising (i) determining in vitro whether the T cells of the individual recognise a protein from said agent having a length of at least 30 amino acids, to a greater extent than one or more peptide epitopes from the agent, a greater extent of recognition of the protein indicating that the individual has recently been exposed to the agent; and (ii) determining whether the T cells of the individual recognise antigen from the mycobacterium at a subsequent second time point, wherein a greater extent of recognition of the protein in (i) and the finding that the T cells do not recognise antigen at the second time point indicates that the individual has been recently exposed to a mycobacterium and has cleared infection by the mycobacterium.

Methods of Diagnosing or Monitoring Before or During Immunosuppressive Therapy

The inventors have realised that detection of latent mycobacterial infection, and therefore of susceptibility to active tuberculosis, in individuals on immunosuppressive therapy may be determined using the T cell based assays described herein.

Accordingly the invention provides a method of diagnosing susceptibility to active tuberculosis disease and latent mycobacterial infection in an individual on or about to start immunosuppressive therapy comprising detecting whether or not the T cells of the individual recognise mycobacterial antigen, wherein recognition of mycobacterial antigen by the T cells indicates susceptibility to active tuberculosis disease and latent mycobacterial infection.

In addition the invention provides a method of monitoring susceptibility to active tuberculosis disease and latent mycobacterial infection in an individual on immunosuppressive therapy comprising detecting whether or not the T cells of the individual recognise mycobacterial antigen, wherein recognition of mycobacterial antigen by the T cells indicates susceptibility to active tuberculosis disease and latent mycobacterial infection.

The individuals who are diagnosed or monitored may be any of the types of individuals who are mentioned herein, but are preferably human.

The immunosuppressive therapy in these methods may comprise administration of an anti-TNF-∀ agent. Such an agent generally counters the effects of TNF-∀. In one embodiment the anti-TNF-∀ agent binds to TNF-∀. Alternatively the anti-TNF-∀ agent may act at the TNF-∀ receptor, and in one embodiment binds the TNF-∀ receptor. In a preferred embodiment the anti-TNF-∀ agent is, or comprises, an antibody or a fragment of an antibody that binds to TNF-∀. Such an agent may be a human or mouse antibody or a chimeric antibody which comprises human antibody sequence. In a preferred embodiment the antibody is a human-murine chimeric antibody. In a highly preferred embodiment the antibody is infliximab (remicade) or humira. The anti-TNF-∀ agent may be, or comprise, a TNF-∀ receptor or fragment of such a receptor, for example etanercept.

The immunosuppressive therapy may comprise administration of anti-methotrexate, azathioprine, a corticosteroid or mycophenolate mofetil immunosuppressive therapy. The individuals may additionally be taking clacineurin inhibitors, such as cyclosporine or tacrolimus. The individuals may be taking functional analogues of methotrexate, azathioprine, a corticosteroid, mycophenolate mofetil, cyclosporine or tacrolimus which are able to cause immunosuppression.

The said determining of T cell recognition may be carried out using any suitable method, such as any suitable method disclosed herein. The mycobacterium may be any such mycobacterium mentioned herein, but is preferably M. tuberculosis. The antigen may be any antigen which is recognised by T cells (such as any type of T cell mentioned herein) and thus may be any of the proteins or peptide epitopes mentioned herein. Analogues of the antigen may be used in the determination such as any of the types of, or specific, analogues mentioned herein.

A kit for carrying out the above methods of diagnosing/monitoring susceptibility to mycobacterial disease/infection is also provided, as well as method of treating individuals who are identified as being susceptible to mycobacterial disease/infection.

Method of Detecting Susceptibility to Onset of Mycobacterial Disease

The invention provides a method of detecting susceptibility to onset of active mycobacterial disease in an individual who does not have any symptoms of mycobacterial disease comprising determining whether the individual has increased levels of T cells which recognise a mycobacterial antigen, to thereby determine whether the individual is susceptible to onset of active mycobacterial disease.

The individuals who are tested may be any of the types of individuals who are mentioned herein, but are preferably human. The determining of T cell level may be carried out using any suitable method, such as any suitable method disclosed herein. The mycobacterium may be any such mycobacterium mentioned herein, but is preferably M. tuberculosis. The antigen may be any mycobacterial antigen which is recognised by T cells (such as any type of T cell mentioned herein) and thus may be any of the proteins or peptide epitopes mentioned herein. Analogues of the antigen may be used in the determination such as any of the types of, or specific, analogues mentioned herein.

The individual may be selected as being susceptible to the onset of disease if the level (frequency) of mycobacterial antigen specific T cells in the individual is at least five-fold higher, such as at least eight-fold or at least ten-fold higher than at a previous time point in the same individual (generally a previous time point when the individual was also latently infected and asymptomatic). Thus the increase in level of such T cells may be an increase of about at least 80 per million peripheral blood mononuclear cells, such as at least 100 per million, 150 per million or 200 per million.

This one embodiment T cells levels are determined at least two points. The first time point which is previous to the above discussed determination of the increase in level of T cells (which herein is defined as determination at the second time may be separated from the second time point by about 3 to 104 weeks, such as about 8 to 52 or 15 to 30 weeks.

Individuals identified by the method as susceptible to onset of disease may be given appropriate therapy, such as administration of an anti-mycobacterial agent. Individuals identified by the method as susceptible to onset of disease may be selected for testing with other diagnostic tests for active mycobacterial disease, such radiological investigations (and then may be given appropriate therapy for the active disease).

A kit for carrying out the method is also provided, as well as method of treating individuals who are identified as being susceptible to the onset of mycobacterial disease.

Sequence of ESAT-6 (SEQ ID NO: 36):

MTEQQWNFAGIEAAASAIQGNVTSIHSLLDEGKQSLTKL

AAAWGGSGSEAYQGVQQKWDATATELNNALQNLARTI

SEAGQAMASTEGNVTGMFA

Sequence of CFP-10 (SEQ ID NO: 37):

MAEMKTDAATLAQEAGNFERISGDLKTQIDQVESTAGSL

QGQWRGAAGTAAQAAVVRFQEAANKQKQELDEISTNIR

QAGVQYSRADEEQQQALSSQMGF

The invention is illustrated by the following Examples:

EXAMPLE 1

Methods

Ex vivo ELISPOT Assays

ELISPOT assays were performed 2-4 hr after venepuncture. Samples were processed and scored by two scientists without reference to personal identifiers or TST results. Peripheral blood mononuclear cells (PBMC) were separated from heparinized blood by standard density centrifugation and washed in RPMI. PBMC were counted in an automated cell counter under a microscope, resuspended in complete medium (R10), and plated at $2.5 \times 10^5$ cells per well in ELISPOT plates pre-coated with catcher anti-FN-γ monoclonal antibody (mAb) (Mabtech, Stockholm, Sweden) and pre-blocked with R10.

Duplicate wells contained no antigen (negative control), phytohaemagglutinin (positive control) (ICN Biomedicals, OH, USA), recombinant ESAT-6 (rESAT-6) or one of 12 different peptide pools derived from ESAT-6 and CFP10. Assays were incubated overnight at 37 C, 5% $CO_2$, and developed the next morning by washing the plates with phosphate buffered saline 0.05% Tween-20 (Sigma, Mo., USA), incubating for 90 min with detector anti-IFN-γ mAb preconjugated to alkaline phosphatase (Mabtech), repeat washing and 15 min incubation with BCIP/NBT$^{PLUS}$ chromogenic substrate (Moss Inc, MD, USA). Plates were air dried after washing in tap water.

Assays were scored in an automated ELISPOT counter with the same settings for all samples. Test wells were scored as positive if they contained a mean of at least 5 spot forming cells (SFCs) more than the mean of the negative control wells, and, in addition, this number was at least twice the mean of the negative control wells. For peptide pools, a positive was defined as response to pools in both arrays as each array contained a full set of peptides. A positive response to pools of ESAT-6-derived peptides, pools of CFP10-derived peptides or rESAT-6 was deemed a positive ELISPOT assay.

Peptides

As previously described, 17 peptides spanning the length of the ESAT-6 molecule and 18 peptides spanning the length of the CFP10 molecule were purchased (Research Genetics, AL, USA). Each peptide was 15 amino acids long and overlapped its adjacent peptide by 10 residues; purity was >70%. Peptides were arranged into 12 pools comprising 2 arrays of 6 pools each where each array contained all 35 peptides from the two molecules in contrasting combinations, so that each peptide was tested in quadruplicate.

Results 124 individuals from an Italian hospital with recent (11 weeks previously) exposure to (and therefore risk of infection with) *M. tuberculosis* were tested using the ELISPOT assay described above. Using the pools of peptides and the whole antigens for both ESAT-6 and CFP-10 only 10 (8%) were found to be positive by tuberculin skin test whereas 34 (27%) were found to be positive using ELISPOT showing that ELISPOT detects infection earlier after exposure. Of the 124 individuals, 35 were health care workers (HCWs), several of whom may have have been previously exposed to *M. tuberculosis* in the distant past, and 89 were mothers and their 11 week old babies, of whom no babies and only very few mothers might have been previously exposed. Of the 18 HCWs who responded to the ELISPOT 11 (61%) responded to whole antigen only. Of the 16 mothers and babies who responded 14 (87.5%) responded responded to whole antigen to a greater extent than than to the pools of peptides. In this case the 16 mothers and babies responded only to whole antigen and did not respond to the pools of peptides.

In contrast in a study of 545 children in a *M. tuberculosis* outbreak at a UK secondary school, where children were exposed to *M. tuberculosis* 4 to 12 months prior to testing by ELISPOT, 133 children responded to whole ESAT-6 or peptides from ESAT-6, and from these only 13 (9.8%) responded to whole ESAT-6 only (compared with the above figures of 61% and 87.5% in the Italian study). This reflects the fact that the children in the UK school were exposed much earlier than the individuals in the Italian study. Therefore the detection of a higher response to whole antigen than to peptides may be used to detect recent exposure to a pathogen.

EXAMPLE 2

Results of Two Stage Testing (Two Test ELISPOT Format) at 3 and 6 Months after *M. tuberculosis* Exposure A T cell recognition based assay (ex vivo ELISPOT) was used to study the dynamics of early infection at the T cell level (in contrast to symptom based infection/disease indicators). The detectable presence in an individual of effector T cells is believed to indicate that the host is currently infected by a pathogen.

The donors were 108 mothers and babies from the Italian hospital study described above. It was found that 61 donors who had tested negative in the ELISPOT assay at 3 months tested negative again at 6 months. In addition 15 donors who had tested positive at 3 months also tested positive at 6 months. However 13 donors who had tested negative at 3 months tested positive at 6 months, and 19 donors who had tested positive at 3 months then tested negative at 6 months. Therefore by the use of assaying T cells of individuals at two time points after exposure two important groups of individuals were identified.

Firstly the 19 donors who tested positive at the first time point and negative at the second time point are individuals initially became infected and then cleared the infection. These individuals will not require treatment. This illustrates the importance of testing a subsequent second time after an initial positive testing when using T cell based diagnosis of infection. Interestingly all 19 of these donors had only tested positive with antigen and not with peptides, implying that if an individual tests positive in an ELISPOT assay using protein antigen and at the same time negative in an ELISPOT using peptides then the individual may be more likely to clear infection. This illustrates the importance of identifying such individuals (and probably testing them at subsequent time points) to determine whether or not they will be likely to require treatment.

Secondly the 13 donors who tested negative at the first time point and positive at the second time point are individuals who have mounted a slower (weaker) T cell response. Such individuals with weaker responses are more likely to fail to control infection, and hence to develop active disease. Thus a T cell based two time point diagnostic test can be used to identify individuals who are more likely to progress to active disease. Clearly it is desirable to target these individuals for therapy. This finding may also be used to identify individuals who mount a slower response to vaccines or to other moieties which induce a cellular response.

EXAMPLE 3

Early Diagnosis of Subclinical Mycobacterial Infection in an Immunosuppressed Individual The ex vivo enzyme-linked immunospot assay for interferon-gamma (ELISPOT) detects T cells that are specific for antigens expressed by *M. tuberculosis*, but absent from *M. bovis* BCG. In recent tuberculosis (TB) contacts, the assay correlates significantly more closely with *M. tuberculosis* exposure than the TST, and, unlike the TST, is independent of BCG vaccination status. Thus, it appears to have a higher sensitivity and specificity than the TST for detecting *M. tuberculosis* infection. This is the first clinical application of this assay to a difficult and common clinical problem: the evaluation of a recent TB contact on immunosuppressive therapy.

A 24 year old female illegal immigrant from Moldova delivered a healthy baby at the University Hospital of Modena, Modena, Italy. Although she was noted to be thin and persistently coughing, chest radiography was delayed until one week after delivery. X-ray and high resolution computed tomography (HRCT) of the lungs were highly suggestive of active pulmonary TB, and when informed of her suspected diagnosis, she provided a full medical history. It now transpired that her fever and cough had been present for four months, but anxiety about her status as an illegal immigrant had prevented her from seeking medical attention earlier. Ten years previously in Moldova, she had been treated for pulmonary TB with 2 unspecified oral drugs for about 2 months. Three sputum samples were strongly positive (3+) for acid fast bacilli on Ziehl-Neelsen (ZN) staining and HIV serology was negative. Standard 4-drug anti-TB therapy was started. Three weeks later, the sputum specimens grew *M. tuberculosis* complex resistant to isoniazid and rifampin. Therapy was therefore switched to a 5-drug regimen (pyrazinamide, moxifloxacin, ethambutol, streptomycin and clofazimine), which resulted in progressive clinical improvement. The duration of her symptoms suggested that she had been infectious for four months; the investigation of her close contacts was therefore a matter of priority.

The most highly exposed contact was her 41-year old husband. He was on long-term immunosuppressive therapy for inactive Crohn's disease with a maintenance dose of azathioprine (150 mg/day). He had no symptoms whatsoever and physical examination was normal. In view of his azathioprine therapy, a complete blood count and differential white cell count were performed, and both were normal. As a close household contact, the husband was considered to be at high risk of infection with multidrug resistant (MDR) *M. tuberculosis;* if infected, he would be at high risk of progression to active MDR TB, on account of his immunosuppressive therapy. However, the limitations of the TST presented some serious obstacles to his management. In particular, the TST is often falsely negative (poor sensitivity) in individuals on immunosuppressive medications, with HIV infection, or with certain chronic illnesses (e.g. chronic renal failure), i.e. precisely those people at greatest risk of progression to active tuberculosis. Early identification of infection with MDR *M. tuberculosis* is especially important, since active, symptomatic MDR TB carries a high mortality. The husband was therefore invited to undergo testing by ELISPOT as well as TST.

TST was administered by the Mantoux method using 5 IU of protein purified derivative (PPD) (Biocine, Chiron Italy). The transverse diameter of cutaneous induration was measured with a ruler and recorded 72 hours after inoculation, using 5 mm as the cut-off for a positive test. Immediately after TST administration, a venous blood sample was taken and the ELISPOT assay performed as previously described, using antigens highly specific for *M. tuberculosis* complex. The antigens used were recombinant early secretory antigenic target-6 (ESAT-6), recombinant culture filtrate protein 10 (CFP10), and peptide pools derived from these antigens.

TST induration was 4 mm, and hence deemed to be negative, whereas the ELISPOT test result was positive. On account of the positive ELISPOT result, the husband underwent chest radiography and HRCT. Chest radiography showed poorly defined non-specific shadowing in the periphery of the upper zone of the right lung and chest HRCT demonstrated several small foci of consolidation, one with very early cavitation. Fiberoptic bronchoscopy with bronchoalveolar lavage (BAL) was performed in the anterior segment of the right upper lobe. Lavage fluid revealed acid-fast bacilli on ZN staining, and the patient was therefore prescribed the same 5 anti-TB drugs as his wife, on the basis of a presumptive diagnosis of MDR-TB. *M. tuberculosis* complex was isolated from BAL fluid cultures 5 weeks later. The drug resistance pattern was the same as the wife's isolate, and molecular strain typing (DNA fingerprinting), using IS6110 restriction fragment length polymorphism analysis, indicated that his isolate was identical to that of his wife.

Clinical application of this novel T cell-based test in the evaluation of a recent TB contact resulted in the early diagnosis and prompt treatment of sub-clinical, active pulmonary MDR TB in an asymptomatic person with a negative skin test. As well as being of direct benefit to the husband, early diagnosis prevented secondary transmission of this MDR *M. tuberculosis* strain in the community. The reason why the ELISPOT assay was able to detect the presence of early subclinical MDR TB where the TST failed to do so may be because ELISPOT assay may be less susceptible than the TST to false negative results in iatrogenically immunosuppressed individuals. A large and increasing number of patients are on medications that cause mild-to-moderate immunosuppression and, as in the case reported here, many have impaired delayed type hypersensitivity responses and falsely negative TSTs. Moreover, it is often precisely these immunosuppressed patients who are more likely to progress to severe and disseminated forms of TB. Screening for asymptomatic *M. tuberculosis* infection is especially critical in patients with autoimmune and inflammatory diseases who are candidates for therapy with anti-TNF-alpha agents (e.g. Infliximab). An important adverse effect of this potent new class of agents is reactivation of TB in latently infected individuals, but diagnosing latent *M. tuberculosis* infection by TST in these patients is especially difficult as most are already on immunosuppressive agents.

We have shown that this novel T cell-based test detected early, active MDR TB in the absence of symptoms and in the setting of a negative TST. Our report demonstrates, for the first time, the clinical utility of a blood test for *M. tuberculosis* infection, and it shows the potential of ELISPOT for improving clinical outcome. On the basis of these results, ELISPOT is currently being used to screen all the hospital contacts of the source case described in this report in order to help prevent a nosocomial outbreak of MDR TB.

EXAMPLE 4

Investigation of Patients with Rheumatoid Arthritis on Immunosuppressive Medications about to Start Infliximab Therapy The Th1 cytokine Tumour Necrosis Factor alpha (TNF-α) is a key cytokine in immunity and inflammation. Monoclonal antibodies that neutralise TNF and drugs that block its receptor are an important new class of drugs for the treatment of chronic autoimmune diseases that are refractory to other medications. Such conditions include rheumatoid arthritis (RA) and Crohn's disease (CD), and Ankylosing Spondylitis (AS) and the list of conditions where these drugs are finding clinical application is increasing and now includes seronegative spodyloarthropathies and sarcoidosis. The first anti-TNF agent to enter clinical practice was Infliximab, a humanised anti-TNF monoclonal antibody. Thus it is with this agent that we have the most experience if clinical efficacy, as well as adverse effects.

Infliximab is safe and well tolerated and the main adverse event is the reactivation of latent tuberculosis (TB) infection (LTBI). 90% of people with LTBI remain healthy life-long; only 10% will develop active TB. However, Infliximab therapy increases this risk many fold, and most patients with LTBI who start Infliximab will develop active TB within 17 weeks of initiating therapy. Reactivation TB can be prevented by taking anti-TB preventative therapy (isoniazid preventative therapy) for 6 months. Doctors prescribing Infliximab are therefore advised by the manufacturer to screen patients for LTBI prior to starting therapy.

The difficulty lies in identifying who actually has LTBI. Until very recently, the only method for diagnosing LTBI was the century-old tuberculin skin test (TST). The TST has some major drawbacks, including low specificity (mainly due to cross-reactivity with *M. bovis* BCG and environmental mycobacteria) and low sensitivity (in fact, there is no gold standard for the diagnosis of LTBI). The main problems faced by physicians who wish to start Infliximab therapy are thus:

False negative TST results (caused by the existing immunosuppressive therapy or indeed the target disease itself). False negative results mean that patients with true LTBI will be missed, will start Infliximab, and then develop reactivation TB False positive TST results (caused by prior BCG-vaccination). False positive results mean that many patients in need of Infliximab will be wrongly denied therapy for fear of reactivating TB, although in reality they do not have LTBI. This is a common problem, as most of the population of Europe and the world is BCG-vaccinated The ELISPOT assay was used to study 10 rheumatoid arthritis patients about to start Infliximab therapy. Despite already being on immunosuppressive therapies (including methotrexate, azathioprine, corticosteroids) these patients still had readily detectable IFN-γ-secreting T cells to positive control antigens in the ELISPOT assay. One of these patients had a past history of household TB exposure. She was positive for TB infection by ELISPOT, but negative by TST. This person's LTBI would therefore have been missed if only TST had been used, but it was detected by ELISPOT. Moreover, 10 weeks after starting Infliximab she remained ELISPOT positive, indicating that ELISPOT can be used to detect LTBI even after a patient has started TNF-blockade therapy.

EXAMPLE 5

Investigation of Effector T Cell Frequency as Predictor of Onset of Tuberculosis Disease The ELISPOT assay was used to examine the change in effector T cell frequency in a patient who progressed from asymptomatic latent tuberculosis infection to active tuberculosis. Onset of symptoms occurred at 8 months after the start of the study, and treatment of disease was started at 10 months. The diagnosis of disease was confirmed by culturing of the mycobacterium. The results are shown below.

| Time point (months) | Effector T cell frequency (SFU's per $10^6$ cells) |
|---|---|
| 0 | 40 |
| 6 | 564 |
| 12 | 216 |

SFU-spot Forming Units

The above data shows that there is a marked increase in effector T cell frequency (at 6 months) before the onset of disease symptoms (at 8 months). The increase in effector T cell frequency probably reflects an increase in the burden of bacilli (i.e. an increase in antigen burden). Although the increase in bacilli leads to an increase in effector T cells it does not cause enough tissue pathology to cause symptoms until the 8 month time point. Therefore detection of effector T cells (for example using ELISPOT) may be used as a predictor of the onset of active tuberculosis.

The invention claimed is:

1. A method of diagnosing in an individual a recent exposure to *M. tuberculosis*, said method comprising:

(a) providing a T cell-containing sample from said individual;

(b) contacting different aliquots of said sample separately with antigen compositions comprising either whole ESAT-6, or peptide epitopes derived from ESAT-6 that are 8 to 29 amino acids in length, in ELISPOT assays in order to determine the frequency of antigen-responsive T cells which have been induced to secrete a cytokine; and (c) evaluating the responsive T cells in each separate ELISPOT assay, wherein a positive response using whole ESAT-6 and a negative response using said peptide epitopes indicates that the individual has recently been exposed to *M. tuberculosis*.

2. A method according to claim 1, wherein said peptide epitopes are 12 to 25 amino acids in length.

3. A method according to claim 1, wherein a pool of at least four different peptide epitopes is employed.

4. A method according to claim 1, wherein said peptide epitopes represent all possible peptide epitopes derived from ESAT-6.

5. A method according to claim 1, wherein antigen presenting cells are present in said sample.

6. A method according to claim 1, wherein said peptide epitopes are selected from the group consisting of:

| | |
|---|---|
| MTEQQWNFAGIEAAA, | (SEQ ID NO:1) |
| WNFAGIEAAASAIQG, | (SEQ ID NO:2) |
| IEAAASAIQGNVTSI, | (SEQ ID NO:3) |
| SAIQGNVTSIHSLLD, | (SEQ ID NO:4) |
| NVTSIHSLLDEGKQS, | (SEQ ID NO:5) |
| HSLLDEGKQSLTKLA, | (SEQ ID NO:6) |
| EGKQSLTKLAAAWGG, | (SEQ ID NO:7) |
| LTKLAAAWGGSGSEA, | (SEQ ID NO:8) |
| AAWGGSGSEAYQGVQ, | (SEQ ID NO:9) |
| SGSEAYQGVQQKWDA, | (SEQ ID NO:10) |
| YQGVQQKWDATATEL, | (SEQ ID NO:11) |
| QKWDATATELNNALQ, | (SEQ ID NO:12) |
| TATELNNALQNLART, | (SEQ ID NO:13) |
| NNALQNLARTISEAG, | (SEQ ID NO:14) |
| NLARTISEAGQAMAS, | (SEQ ID NO:15) |
| ISEAGQAMASTEGNV, and | (SEQ ID NO:16) |
| QAMASTEGNVTGMFA. | (SEQ ID NO:17) |

* * * * *